United States Patent [19]

Hendry

[11] 4,169,368
[45] Oct. 2, 1979

[54] ADJUSTABLE LUBRICATION QUALITY INDICATOR-PROTECTOR FOR ENGINES AND OTHER MACHINES

[76] Inventor: Harold M. Hendry, P.O. Box 13228, Tampa, Fla. 33611

[21] Appl. No.: 912,999

[22] Filed: Jun. 6, 1978

[51] Int. Cl.² .................... G01N 19/00; G01N 33/30
[52] U.S. Cl. .......................................... 73/10; 73/64
[58] Field of Search .................. 73/53, 10, 64, 61.1 R

[56] References Cited

U.S. PATENT DOCUMENTS

| | | | |
|---|---|---|---|
| 134,229 | 12/1872 | Thurston | 73/10 X |
| 226,639 | 4/1880 | Waite | 73/10 |
| 230,158 | 7/1880 | Thurston | 73/10 X |
| 332,974 | 12/1885 | Thurston | 73/10 X |
| 1,490,603 | 4/1924 | Elverson | 73/10 X |

FOREIGN PATENT DOCUMENTS 865390 2/1953 Fed. Rep. of Germany .............. 73/10

*Primary Examiner*—Gerald Goldberg
*Assistant Examiner*—Joseph W. Roskos
*Attorney, Agent, or Firm*—Stein & Frijouf

[57] ABSTRACT

A device is disclosed for indicating the lubricating quality of a lubricating oil for a machine. The device comprises a frame rotatably mounting a shaft. The rotatable shaft has a journal for rotation with the shaft. A housing having an internal cavity is rottably mounted on the rotatable shaft with the journal disposed within the internal cavity of the housing. A journal-engaging member is mounted in the internal cavity for engaging the journal to establish a normal force between the journal-engaging member and the journal. An oil outlet and an oil inlet communicate with the internal cavity in the housing. The oil inlet and oil outlet are connected to a machine for circulating lubricating oil between the housing and the machine whereby the lubricating oil is directed between the journal and the journal-engaging member. A retarding means retards the rotation of the housing relative to the frame with indicating means indicating the rotational position of the housing relative to the frame to determine the quality of the lubricating oil from the torque transfer of the rotating shaft to the housing by friction between the journal and the journal-engaging means.

10 Claims, 9 Drawing Figures

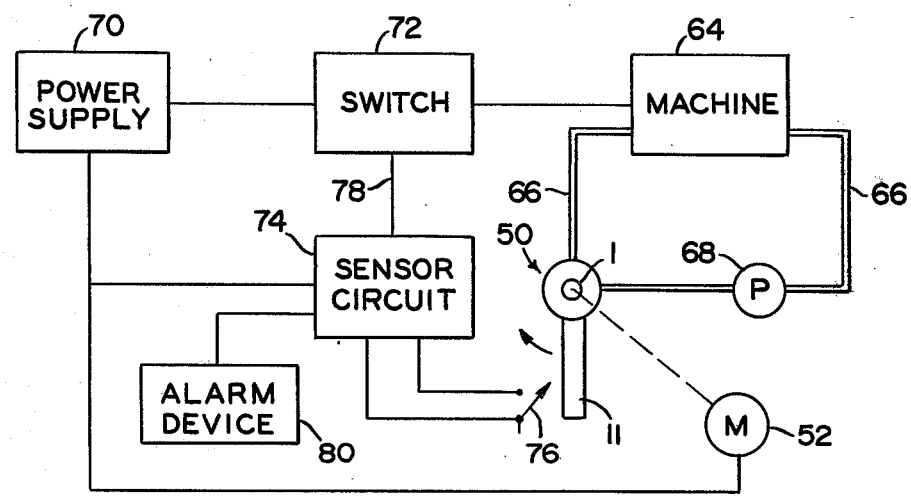
FIG. 8
FIG. 9
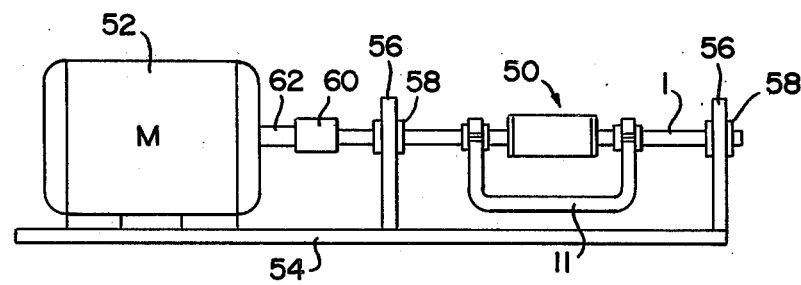

ADJUSTABLE LUBRICATION QUALITY INDICATOR-PROTECTOR FOR ENGINES AND OTHER MACHINES

BACKGROUND OF THE INVENTION

1. Field of the Invention

This invention relates to a device for indicating failure of the lubricating capability of oil circulating through a machine requiring high-performance lubrication, and where necessary, shutting down the machine or sounding an alarm before it is damaged by poor lubrication. Examples of machines requiring high-performance lubrication include internal combustion engines, air compressors, gear boxes and other close tolerance mechanisms.

2. Description of the Prior Art

It is well known that running a machine in which wate or fuel has been mixed with the oil will irreparably damage the bearing surfaces of the machine in a relatively short period of time. Many industrial engines, i.e., those used on marine machinery and the like, are not only very expensive, but are used under adverse conditions including continuous heavy duty service by hired operators who often fail to perform simple lubrication maintenance on the machinery.

Failure of a minor part of the machine may cause a rapid deterioration of the lubricating oil. Deterioration of the lubricating oil may, in turn, cause major and costly damage to the entire machine unless detected early by the operator.

There is no known device in the prior art which is designed to protect machines from poor lubrication, indicate lubrication quality and which has provision for adjusting friction sensitivity.

Therefore, it is an object of this invention to provide an apparatus which overcomes the aforementioned inadequacies and provides a significant contribution to the advancement of the lubricating art.

Other objects and a fuller understanding of this invention may be had by referring to the summary of the invention, the description and the claims, taken in conjunction with the accompanying drawings.

SUMMARY OF THE INVENTION

The device of this invention is comprised of a rotatable shaft with concentric or eccentric journal, and a cylindrical journal-engaging member mounted thereon and permitting the journal to rotate therein. The surface between the journal and journal-engaging member is lubricated with the lubricating oil to be tested. End bearings rotatably mount the journal-engaging member on said journal with a mechanical connection causing rotation of said journal. The pressure on the lubricated surface between said journal and journal-engaging member is adjustable in proportion to the rotational friction forces between said journal and said journal-engaging member to provide a visual indication of said rotational frictional force. A cutoff or sounding of an alarm may be provided when the rotational frictional force exceeds an adjustably defined value. An alternate embodiment of the invention utilizes a rotating disc member and a fixed disc member rather than a journal and journal-engaging member.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 8 is a block diagram of a complete system incorporating the invention; and

FIG. 9 is an illustration of the invention driven by an external motor.

Similar reference characters refer to similar parts throughout the several views of the drawings.

DETAILED DESCRIPTION

Figure 1:
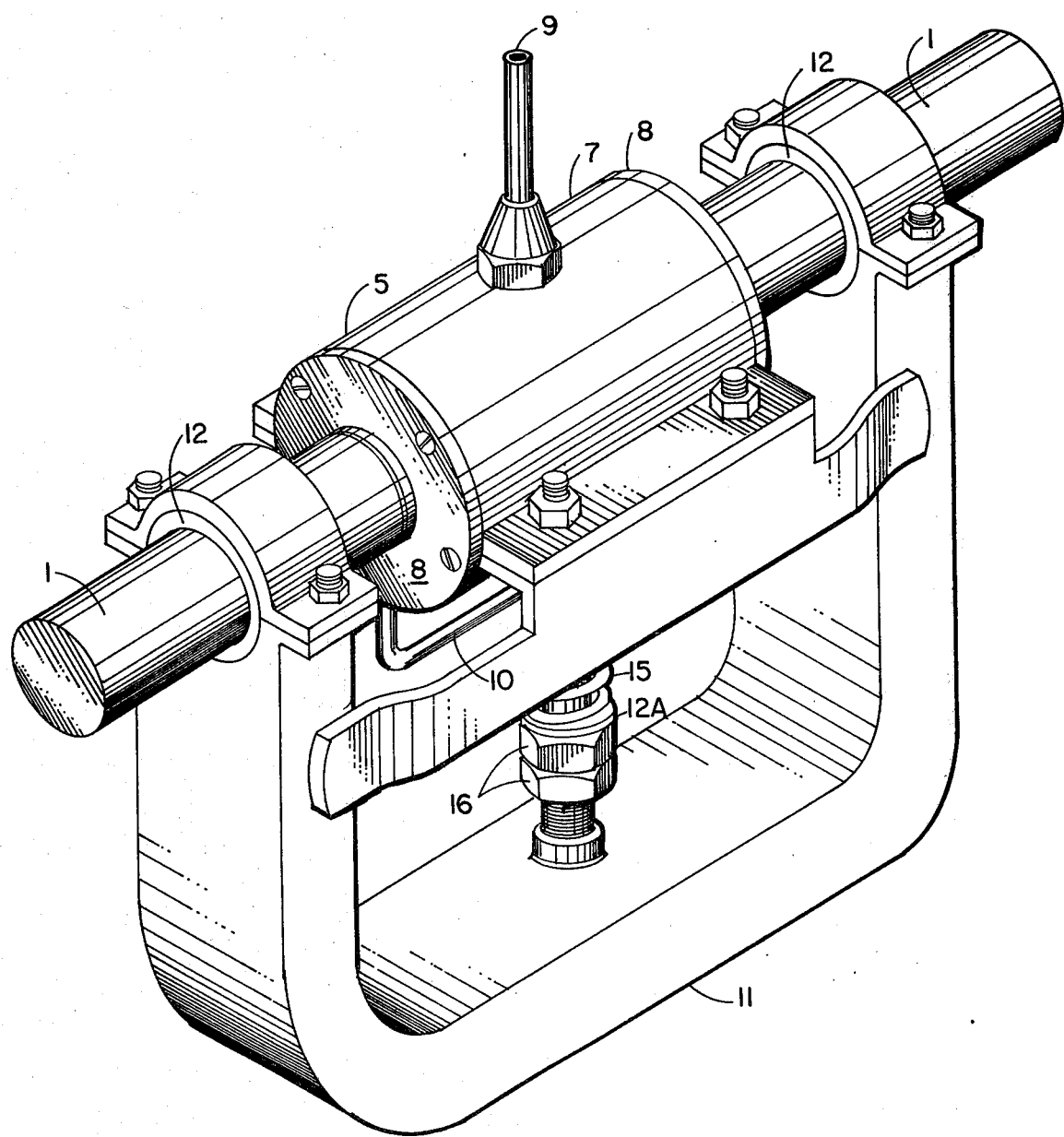
FIG. 1 is an isometric view of the device of this invention in a first embodiment.
Figure 2:
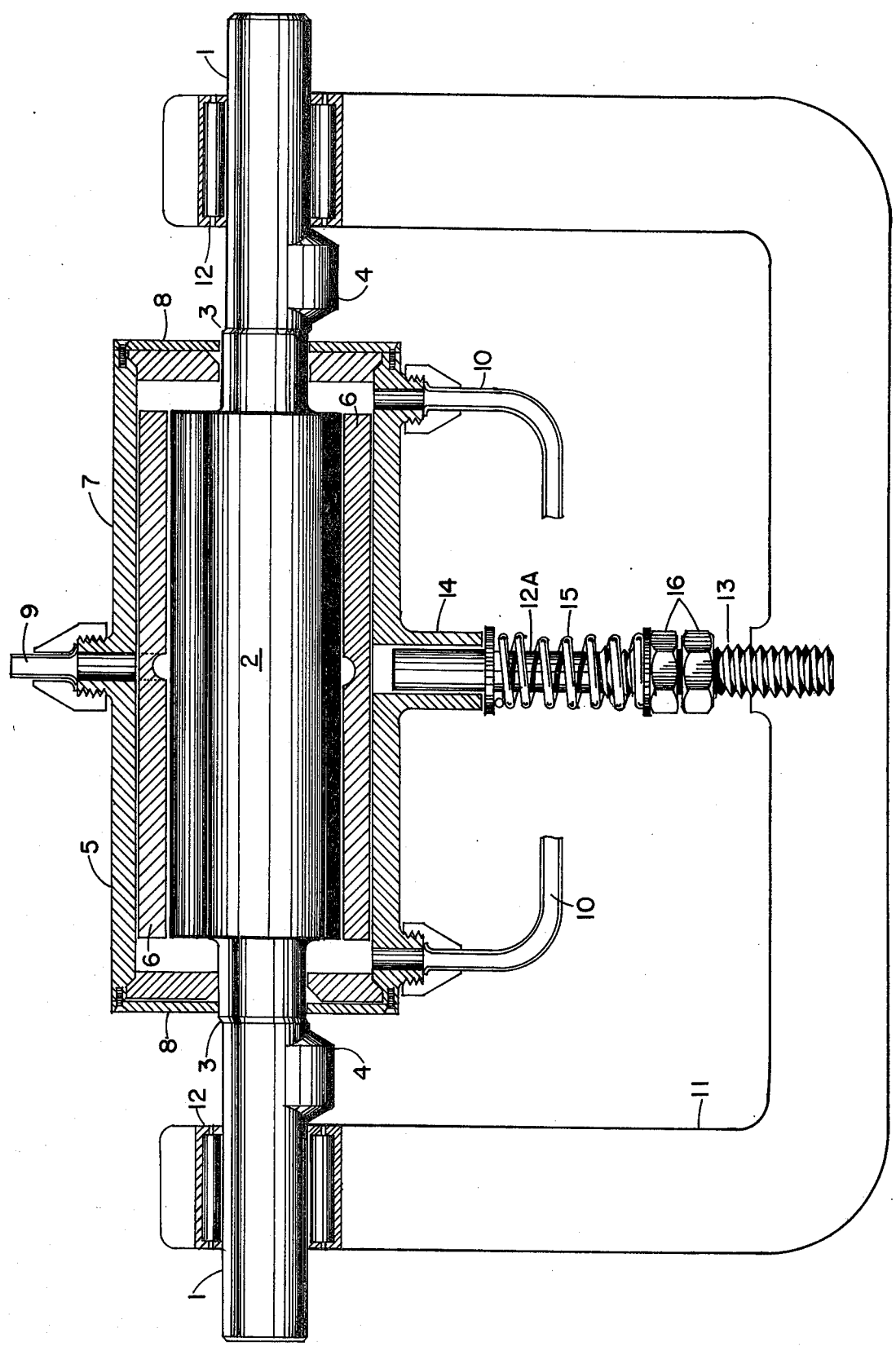
FIG. 2 is a side cross-sectional view of the first embodiment illustrated in FIG. 1.
Figure 3:
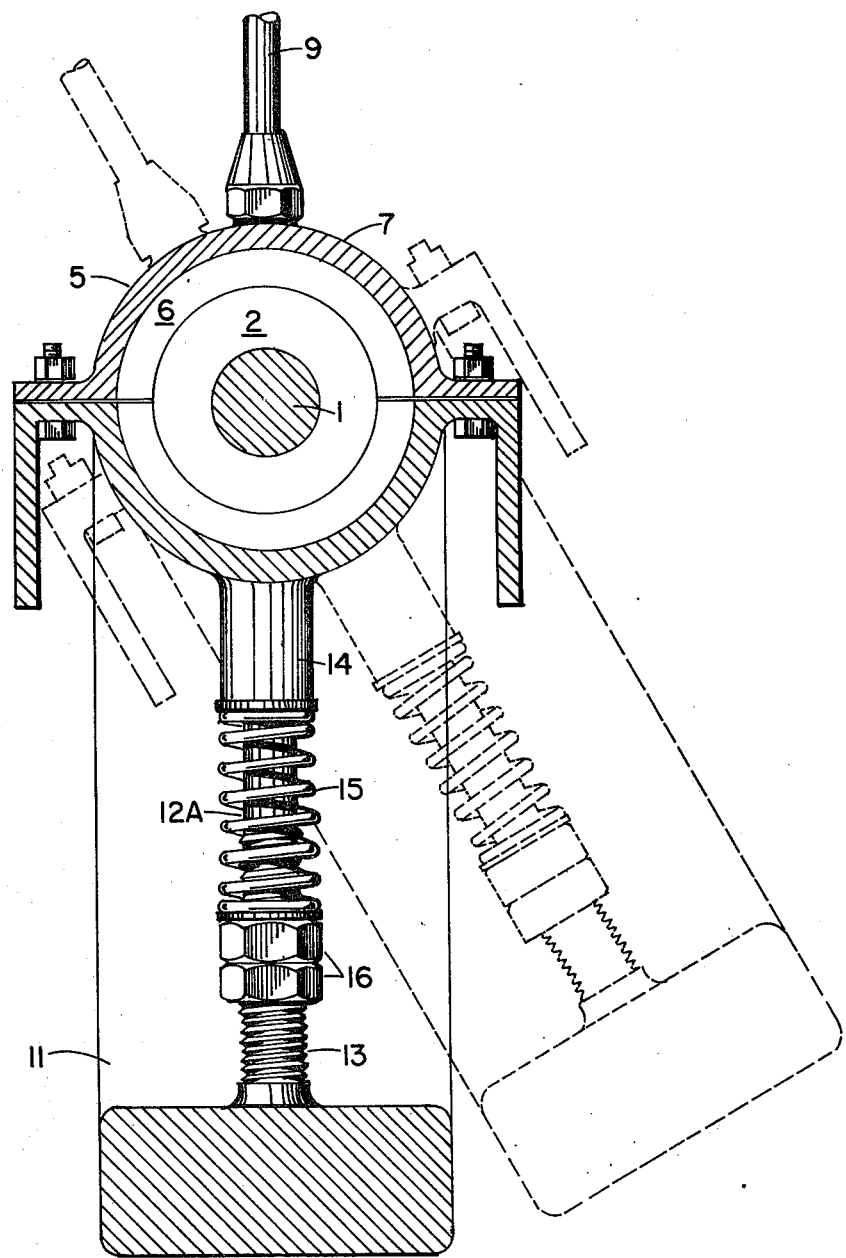
FIG. 3 is an end cross-sectional view of the first embodiment illustrated in FIG. 1.

Referring to FIGS. 1, 2 and 3, steel shaft 1 is driven by the machine or engine to be protected by the device or by an independent driver such as an electric motor. Mechanical connection may be through any suitable means including a belt or a gear arrangement. The shaft is mounted in fixed relationship to the machine or engine by bearings (not shown). These bearings are preferably located near the ends of the shaft. In another configuration, the device of this invention may be mounted vertically on a thrust bearing. The many mounting methods are obvious to those skilled in the art.

Shaft 1 is formed integrally with journal 2. Shaft 1 and journal 2 may be constructed with either a concentric or eccentric relationship between their respective center lines. FIG. 2 illustrates a construction with an eccentric relationship between shaft 1 and journal 2, the center line relationship being indicated by offset 3. The offset journal 2 is counterbalanced by weights 4 attached to the opposite side of shaft 1. Offset 3 is sufficient in magnitude to create a dynamic loading of the bearing surface between journal 2 and journal-engaging member 5, which surrounds journal 2 and is slightly greater in diameter than journal 2. For example, offset 3 may be approximately 0.010 inch for use with a journal 2 in the range of two inches in diameter. Eccentric journal 2 is used where the device is constructed to stimulate the action of rod bearings found in machines containing pistons. Journal-engaging member 5 may consist of insert bearings 6 similar to those commonly used in construction of crankshaft bearings of internal combustion engines. Insert bearings 6 are of the split type and are designed to fit with close tolerance in housing 7. Housing 7 is also split in the well-known manner and is provided with gaskets and shaft seals 8 to prevent oil from escaping.

Oil from the machine to be monitored by the device is fed under pressure from an oil pump into oil inlet means 9. Oil inlet means 9 may consist or a flanged pipe with coupling threaded to match that of a matching hole in housing 7. The location of the hole in housing 7 is such that oil flows into the center slot of insert bearing 6, then out the ends of journal 2. The oil is then collected at the bottom of housing 7, where it is returned to the oil reservoir of the machine through oil outlets 10, which also may consist of flanged pipes with couplings threaded to match holes in housing 7.

Housing 7 is attached to rotating arm 11. Rotating arm 11 may be restricted to partial rotation by its own weight and by attachment of incremental weights. It is also apparent to those with mechanical skill that rotating arm 11 may be restricted to partial rotation through use of springs.

Rotating arm 11 is attached to shaft 1 by means of two roller bearings 12 positioned on either side of housing 7. During operation, the rotation of shaft 1 and journal 2 will cause transmission of a torque to rotating arm 11 with the torque being primarily proportional to the frictional forces on journal-engaging member 5. These frictional forces will be proportional to the quality of lubrication primarily and the speed of rotation secondarily. Loss of machine oil quality causes increased frictional force between journal 2 and journal-engaging member 5. The resultant increased torque on rotating arm 11 causes a proportional rotation of said arm. The extent of rotation is determined by the weight of arm 11 or the strength of a spring used to restrain the arm. The extent of rotation also provides visual indication to the machine operator of oil quality. Alternate means of visual indication may be provided by mechanical or electro-mechanical connections to transmit the extent of rotation of arm 11 to an indicating gauge on the operator control panel.

An electrical switch, not shown, may be positioned with respect to arm 11 such that arm 11 will operate the switch if unsatisfactory oil quality causes increased torque with resulting rotation of arm 11. The switch in turn, may be electrically connected to illuminate a warning light, to sound an alarm or to cause the machine to cease running. Installations of this nature are well-known to those skilled in the art pertaining to this invention.

Rotating arm 11 is provided with pressure adjusting means 12A which is used to increase or decrease the frictional force between journal 2 and journal-engaging member 5. In the preferred embodiment, pressure adjusting means 12A is comprised of a threaded spring guide 13 rigidly attached to arm 11 and extending toward and into an aperture 14 in housing 7. A coil spring 15 surrounds guide 13, and a pair of locking nuts 16 surround guide 13. Locking nuts 16 are rotated to increase or decrease spring compression, thereby increasing or decreasing the frictional force between journal 2 and journal-engaging member 5. This device will be adjusted to be more sensitive to proper lubrication than any of the bearings in the monitored machine. Therefore, the device will contain the first of all of the bearings to indicate unsatisfactory lubrication and will be the only bearing to indicate high frictional characteristics by simple visual observation and/or by connecting devices heretofore explained.

Figure 4:
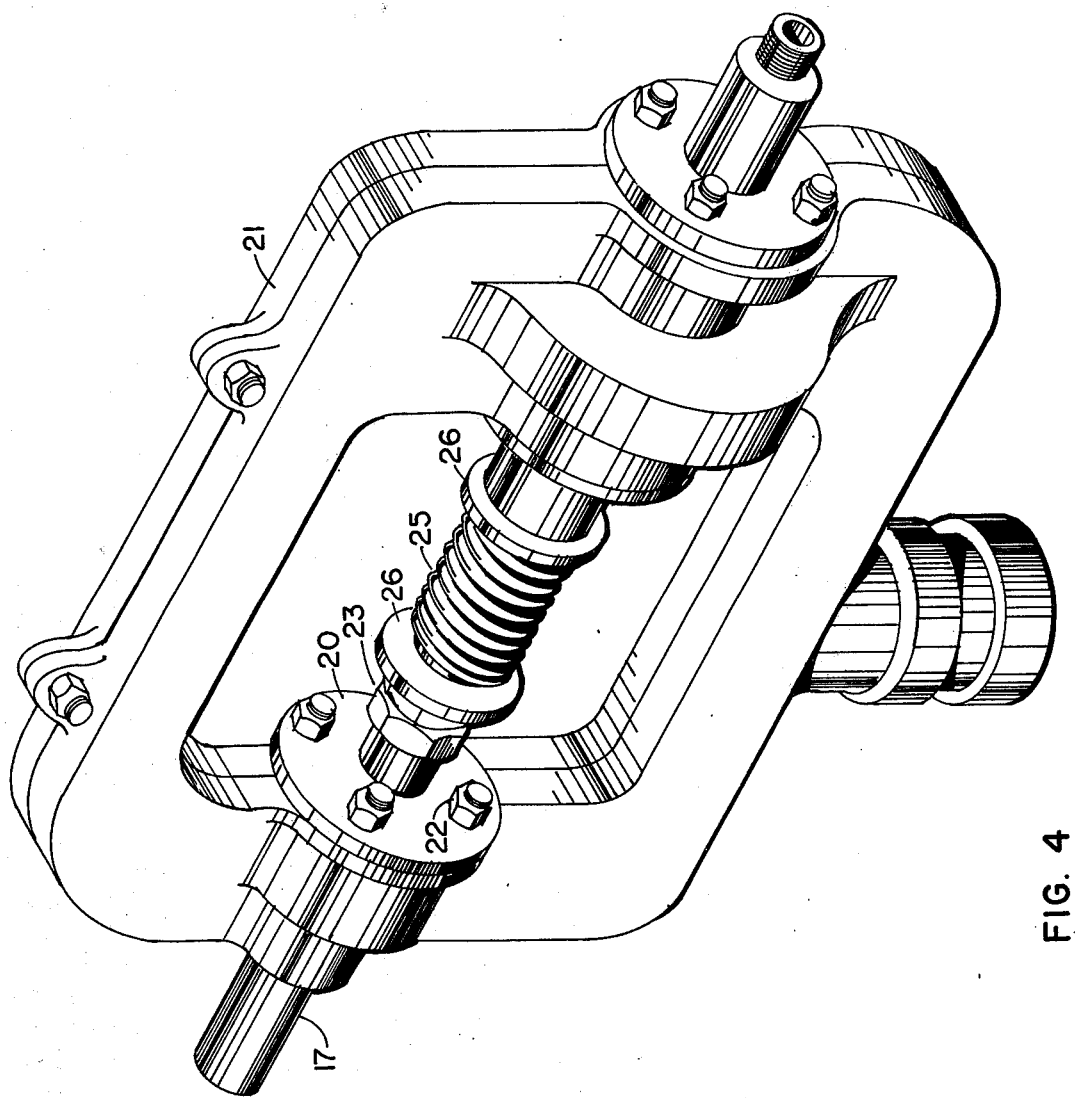
FIG. 4 is an isometric view of a second embodiment of the device of this invention.
Figures 5, 6:
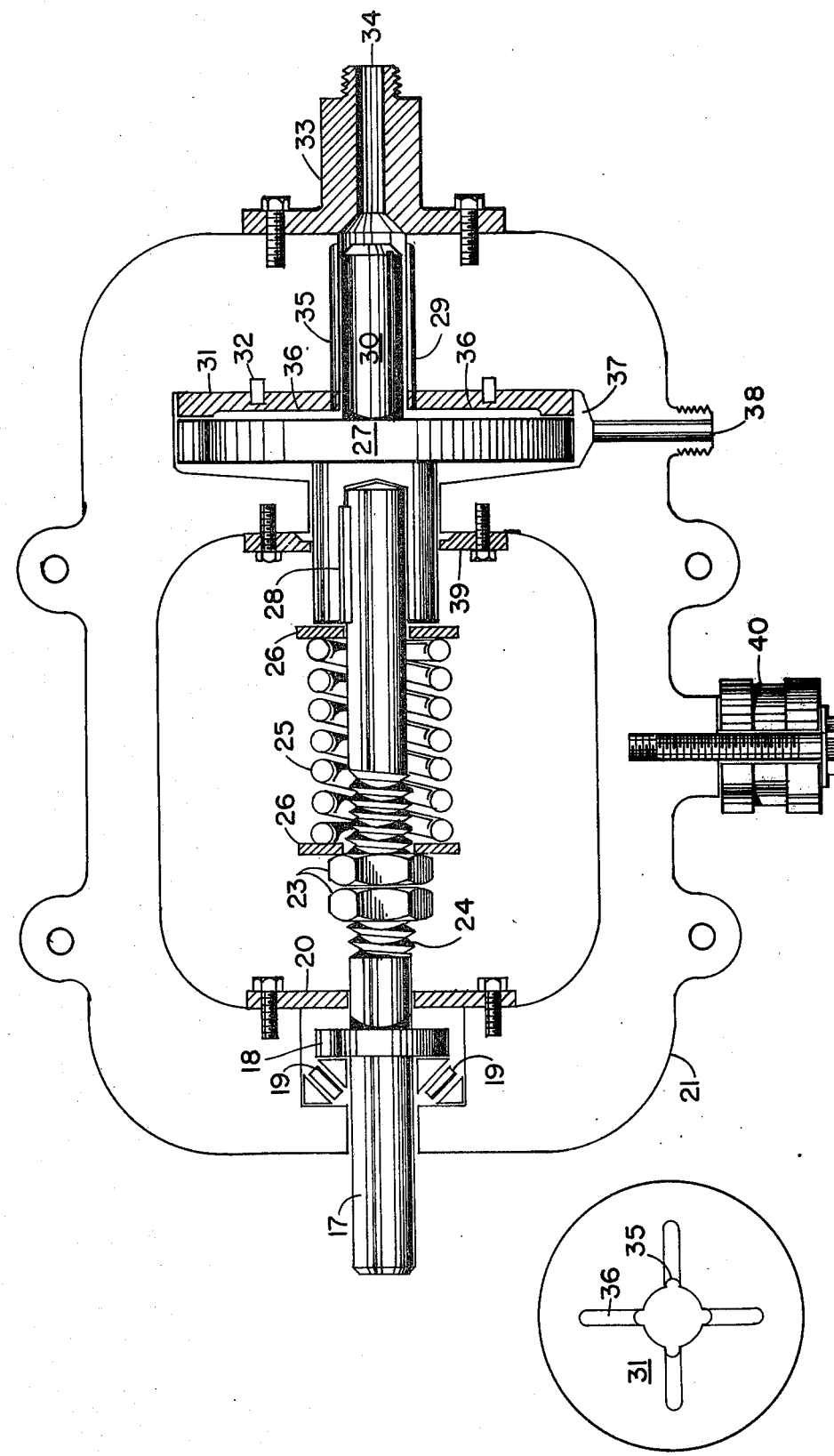
FIG. 5 is a side cross-sectional view of the second embodiment illustrated in FIG. 4.
FIG. 6 is an end view of the fixed thrust plate of the embodiment shown in FIG. 5.

Referring to the second embodiment as indicated in FIGS. 4, 5 and 6, steel shaft 17 is driven by means similar to those described for the first embodiment. Shaft 17 is constructed with thrust ring 18 which rotates against thrust radial bearing 19. Cover plate 20 is attached to split housing 21 by bolts 22. Pressure on the test bearing surfaces is adjusted by means of a pair of locking nuts 23 which may be rotated on a threaded part 24 of shaft 17, thereby compressing spring 25 between washers 26. Rotating thrust plate 27 is slidably attached to shaft 17 by means of slot and key 28. Rotating thrust plate 27 is fixed in rotating position by pilot bearing 29 and pilot shaft 30 in split housing 21. During operation, rotating thrust plate 27 is pressed against fixed thrust plate 31 which is prevented from rotating with respect to split housing 21 by dowels 32. Lubricating oil flows through hole 34 in end housing 33 to the end of pilot shaft 30, then through grooves 35 along the length of pilot bearing 28 and into a plurality of radial slots 36 imbedded in fixed thrust plate 31. The oil is collected in reservoir 37 and flows out through outlet 38 to return to the machine or engine which is monitored by the device. Cover plate 39 with seal (not shown) is attached to split housing 21 to prevent oil from leaving the reservoir through entrance of rotating thrust plate 27 into said reservoir. Operation is similar to that of the first embodiment. A decrease in the quality of oil passing between rotating thrust plate 27 and fixed thrust plate 31 causes split housing 21 to rotate with respect to the normal position. The extent of said rotation may be limited by varying the weight of arm 40 or by use of springs. The sensitivity of the device may be adjusted by movement of locking nuts 23. The device may be used in conjunction with an electrical switch or warning devices as previously described.

An end view of fixed thrust plate 31 is indicated in FIG. 6.

Figure 7:
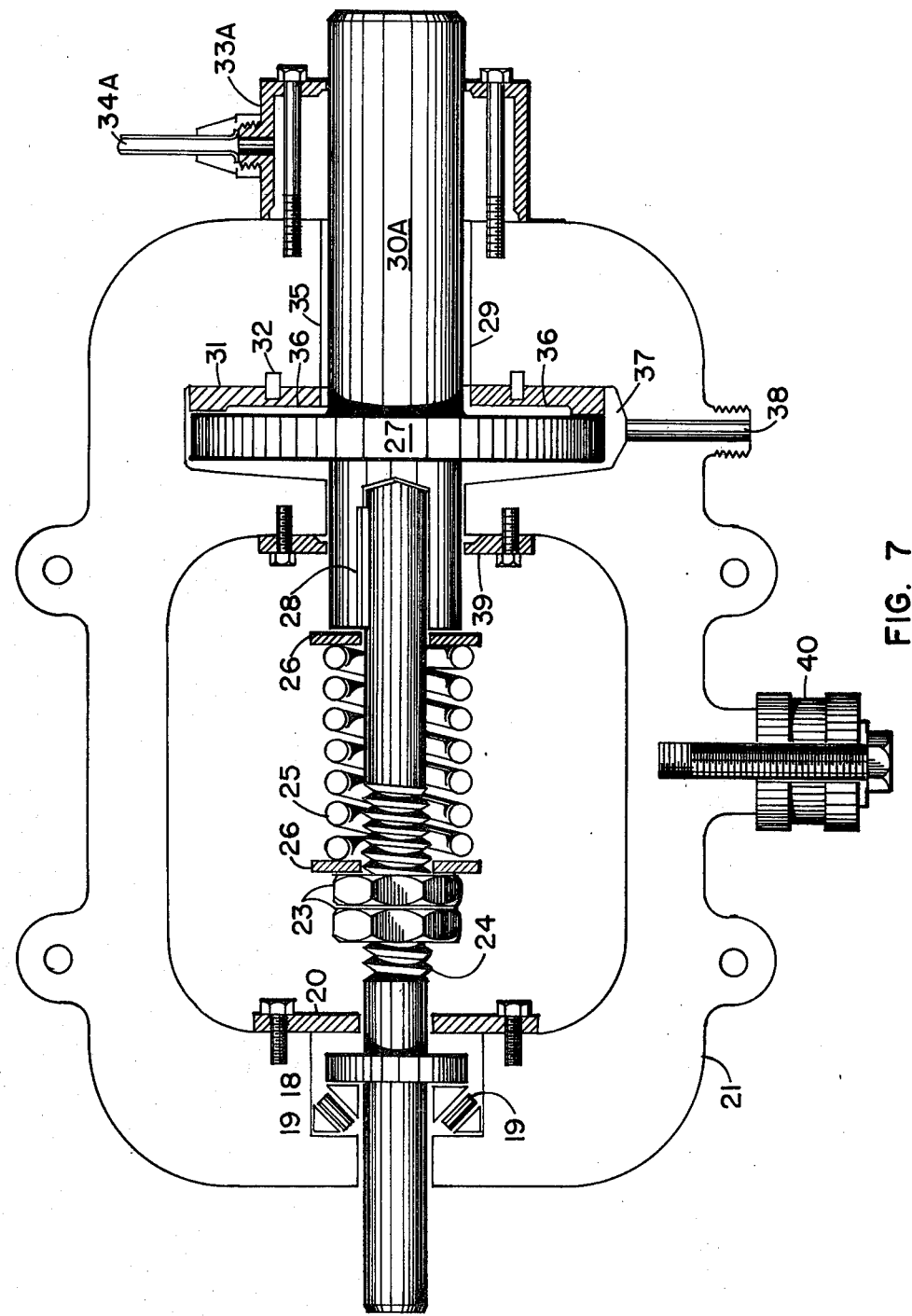
FIG. 7 is a side cross-sectional view of an alternative second embodiment of the device illustrated in FIGS. 4 and 5.

A variation of the second embodiment is shown in FIG. 7. Pilot shaft 30A extends through the end of end housing 33A. Oil undergoing test is forced in hole 34A located in the side of end housing 33A. The variation allows the device to be driven from either end.

The device of this invention may be installed on machines of any type or size. The adjustments for frictional pressure and rotating arm weight allow measurement of oil quality to be made with one device for a large variety of machines.

FIG. 8 is a block diagram of an entire system incorporating the invention shown in FIGS. 1-7. FIG. 9 illustrates the interconnection of the device 50 and an independent drive motor 52. The drive motor 52 is mounted on a frame 54 comprising upstanding frame elements 56 which journal shaft 1 through bearings 58. Shaft 1 is connected through coupling 60 to motor shaft 62 to rotate shaft 1 in accordance with the rotation of motor 52.

FIG. 8 illustrates the device 50 connected to a machine 64 having an oil lubricant circulated to device 50 by conduits 66 and pump 68. A power source 70 supplies electrical power through a switch 72 to machine 64. A sensor circuit 74 is connected to a switch 76 or other sensor disposed adjacent the device 50 for closing switch 76 upon rotation of rotating arm 11 as indicated by the arrow. This rotation occurs if the lubricating quality of the machine oil is reduced below a predetermined standard. The sensor circuit is connected through a connector 78 to deactivate switch 72 to terminate operation of machine 64. An alarm device 80 is simultaneously activated upon closing of the switch 76.

It should be appreciated that the aforementioned system disables the machine 64 as well as activates alarm device 80 upon the device 50 detecting a substandard quality of lubricating oil within the machine 64. The switch 76 may be photo-optical, magnetic, position, a micro-switch or the like. Such devices are considered to be equivalent of that disclosed in the instant specification.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,
I claim:

1. A device for indicating the lubricating quality of lubricating oil for a machine; comprising in combination;
   a frame rotatably mounting a shaft;
   said rotatable shaft having a journal for rotation with said shaft;
   a housing having an internal cavity;
   means for rotatably mounting said housing on said rotatable shaft with said journal disposed within said internal cavity of said housing;
   a journal engaging member mounted in said internal cavity for engaging said journal;
   means for establishing a normal force between said journal engaging member and said journal;
   an oil inlet and an oil outlet communicating with said internal cavity in said housing;
   means connecting said oil inlet and said oil outlet to the machine for circulating the lubricating oil between said housing and the machine;
   said oil inlet and said oil outlet directing the lubricating oil between said journal and said journal engaging member;
   means for retarding the rotation of said housing relative to said frame; and
   means for indicating the rotational position of said housing relative to said frame to determine the quality of the lubricating oil from the torque transferred from said rotating shaft to said housing by friction between said journal and said journal engaging means.

2. A device as set forth in claim 1, wherein said means for retarding the rotation of said housing comprises an arm secured to said housing and extending radially outward relative to said shaft; and
   said frame mounting said shaft in a substantially horizontal plane whereby the force of gravity acts upon said arm to retard the movement of said housing about said shaft.

3. A device as set forth in claim 1, wherein said means for establishing a normal force comprises a spring bias for urging said journal engaging means against said journal; and
   a threaded fastener for adjusting the tension of said spring to vary the normal force between said journal engaging means and said journal.

4. A device as set forth in claim 1, wherein said journal includes a substantially cylindrical surface; and
   said journal engaging means comprising a partially cylindrical member for contacting the outer cylindrical surface of said journal.

5. A device as set forth in claim 1, wherein said journal includes a thrust ring; and
   said journal engaging means comprising a thrust plate for contacting a side of said thrust plate.

6. A device as set forth in claim 1, wherein said means for retarding the rotation of said housing comprises a U-shaped arm having plural terminating ends secured to said housing with the remainder of said U-shaped arm extending radially outwardly relative to said shaft;
   said frame mounting said shaft in a substantially horizontal plane whereby the force of gravity acts upon said arm to retard the movement of said housing; and
   said means for rotatably mounting said housing to said shaft comprising bearing means for journalling said plural terminating ends of said U-shaped arm relative to said shaft.

7. A device as set forth in claim 6, wherein said means for establishing a normal force comprises a thread component in combination with a bias spring extending substantially perpendicular between said shaft and said U-shaped arm.

8. A device as set forth in claim 6, wherein said means for establishing a normal force comprises a threaded component in combination with a bias spring extending substantially parallel to said shaft.

9. A device as set forth in claim 1, including sensor means for sensing the position of said housing relative to said frame; and
   said sensor means providing an electrical output signal upon said housing exceeding a preselected rotational position.

10. A device as set forth in claim 9, including means for terminating operation of the machine upon an electrical output indicator signal from said sensor means.

* * * * *

UNITED STATES PATENT AND TRADEMARK OFFICE
CERTIFICATE OF CORRECTION

PATENT NO. : 4,169,368

DATED : October 2, 1979

INVENTOR(S) : Harold M. Hendry

It is certified that error appears in the above-identified patent and that said Letters Patent are hereby corrected as shown below:

In the Abstract, line 5, delete "rottably" and insert -- rotatably --;

Column 1, line 19, delete "wate" and insert -- water --.

Signed and Sealed this

Twenty-ninth Day of January 1980

[SEAL]

Attest:

SIDNEY A. DIAMOND

Attesting Officer

Commissioner of Patents and Trademarks